United States Patent [19]

Wang et al.

[11] Patent Number: 5,011,678

[45] Date of Patent: Apr. 30, 1991

[54] COMPOSITION AND METHOD FOR ADMINISTRATION OF PHARMACEUTICALLY ACTIVE SUBSTANCES

[75] Inventors: Yu-chang J. Wang; William A. Lee, both of Los Altos; Blair Narog, Palo Alto, all of Calif.

[73] Assignee: California Biotechnology Inc., Mountain View, Calif.

[21] Appl. No.: 305,520

[22] Filed: Feb. 1, 1989

[51] Int. Cl.⁵ .................. A61K 9/12; A61K 9/14; A61K 37/02
[52] U.S. Cl. .................................. 424/45; 514/2; 514/3; 514/171; 514/808; 514/866; 514/922; 514/947; 514/951; 514/958; 514/975
[58] Field of Search ............ 514/958, 947, 2, 3, 514/171, 808, 866, 922, 941, 951, 958, 975; 424/45

[56] References Cited

U.S. PATENT DOCUMENTS

| 4,548,922 | 10/1985 | Carey et al. | |
|---|---|---|---|
| 4,746,508 | 5/1988 | Carey et al. | |
| 4,752,425 | 6/1988 | Martin et al. | 264/4.6 |
| 4,789,660 | 12/1988 | Enever et al. | 514/4 |

FOREIGN PATENT DOCUMENTS

| 0200383 | 12/1986 | European Pat. Off. | 514/958 |
|---|---|---|---|
| 0257956 | 3/1988 | European Pat. Off. | 514/958 |
| 360340 | 3/1990 | European Pat. Off. | |
| 261096 | 10/1988 | German Democratic Rep. | 514/958 |
| 60-161924 | 8/1985 | Japan | 514/958 |
| 63-211237 | 9/1988 | Japan | 514/958 |
| 8707504 | 12/1987 | PCT Int'l Appl. | 514/958 |
| 8800829 | 2/1988 | PCT Int'l Appl. | 514/958 |
| 8801864 | 3/1988 | PCT Int'l Appl. | 514/958 |
| 2193891 | 2/1988 | United Kingdom | 514/958 |

OTHER PUBLICATIONS

Ayer, Antiseptic, 51:1161-1167 (1954).
Govinda-Rao, Indian J. Physiol. Pharmacol., 3:161-167 (1959).
Lee et al., J. Pharm. Sci., 65(4):567-572 (1976).
Wigley et al., Diabetes, 20:552-556 (1971).
Yalow et al., Methods Biochem. Anal., 12:69-96 (1968).
G. S. M. J. E. Duchateau et al., Int. J. Pharm., 39: 87-91 (1987).
J. P. Longenecker et al., J. Pharm. Sci., 76 (5): 351-355 (1987).
W. A. Lee et al., "Intranasal Bioavailability of Insulin Powder Formulations...", submitted to J. Pharm. Sci., in press.
Longenecker et al, C.A. 107:83791k (1987).
Duchateau et al, C.A. 107:242511n (1987).
Su et al, C.A. 106:162571w (1986) of EP 200383, Dec. 10, 1986.
Ueda et al, C.A. 104:10621h (1986) of JP 60/161924, Aug. 23, 1985.
Martin et al, C.A. 110:121402r (1989) of PCT WO88/01,864, Mar. 24, 1988.

Primary Examiner—Shep K. Rose
Attorney, Agent, or Firm—Irell & Manella

[57] ABSTRACT

Pharmaceutically active substances are administered in aerosol form by applying to a mucosal surface of the body a composition comprising a medically effective amount of a pharmaceutically active substance, a biocompatible amphiphilac steroid and a bicompatible (hydro/fluoro)carbon propellant.

43 Claims, 2 Drawing Sheets

COMPOSITION AND METHOD FOR ADMINISTRATION OF PHARMACEUTICALLY ACTIVE SUBSTANCES

BACKGROUND OF THE INVENTION

This invention relates to the field of pharmaceutical administration. More particularly, the invention relates to compositions and methods for the administration of pharmaceutically active substances by permeation of mucosal surfaces of the body such as the mucosal linings of the nasal cavity or the bronchopulmonary system.

The mode of administration of a pharmaceutical product can have a very significant effect on the bioavailability and pharmacokinetics of the product. Furthermore, the mode of administration can have a significant effect on patient compliance inasmuch as patients are more likely to comply with medication regimens when the mode of administration is convenient and comfortable. The effect of the mode of administration on patient compliance is particularly strong where the patient must self-administer the drug on a chronic basis, e.g. in the case of insulin.

In terms of convenience and comfort, oral administration is generally the most preferred method. Unfortunately, many drugs cannot be administered orally due to extensive degradation of the drug which occurs in the gastrointestinal tract before the drug is transferred into the general circulation. Protein and polypeptide drugs are particularly prone to being degraded in the gastrointestinal tract by various hydrolytic and enzymatic means. Accordingly, protein and polypeptide drugs are generally not orally administrable.

The advent of recombinant DNA technology in recent years has made it possible to produce on a commercial scale virtually any polypeptide or protein whose structure has been elucidated. These include a multitude of substances which have great potential pharmaceutical value, but which were previously available from natural sources only in minute quantities suitable solely for research purposes Now that these protein and polypeptide drugs can be produced on a commercial scale, the inability to administer them in a convenient and comfortable manner is one of the few barriers to their becoming staple items of the pharmaceutical armamentarium for fighting or preventing disease. Until fairly recently, the only broadly applicable means for delivering protein or peptide drugs were the parenteral routes.

The aerosol administration of insulin to animals and humans via the respiratory system has been reported by several groups (Ayer, A. A., Antiseptic, 51, 1161 [1954]; Govinda-Rao, A. R., Indian J. Physiol. Pharmacol., 3, 161 [1959]; Wigley, F. M. et al., Diabetes, 20, 552 [1971]; Yalow, R. S. and Berson, S. A., Methods Biochem. Anal., 12, 69 [1968]). Shih-Wei Lee and John J. Sciarra reported the preparation of aerosol dosage forms containing insulin, fluorocarbon propellant and oleyl alcohol (to improve insulin suspension), however, no bioavailability results were given (*J. Pharm. Sci.*, 65, No. 4, 567 [1976]). Unfortunately, due to the low level of bioavailability of aerosol-administered insulin, these delivery systems have not come into therapeutic use.

Recently, Martin Carey and coworkers developed a system for delivering drugs, particularly proteins and polypeptides, by intranasal or other transmucosal routes using low toxicity permeation enhancers of the amphiphilic steroid family, e.g. fusidic acid derivatives to promote efficient transport of the drug across the mucosal surface (U.S. Pat. Nos. 4,548,922 and 4,746,508). The disclosed compositions, which are generally water-based, have been demonstrated to be useful for the intranasal delivery in humans and animals of a variety or proteins and peptides, including insulin, human growth hormone, salmon calcitonin, histerelin (an analogue of luteinizing hormone releasing hormone) and $\beta$-endorphin.

In the aqueous composition of Carey et al. the fusidic acid derivative is present at a concentration above its critical micellar concentration. It is believed that the fusidic acid derivative forms micelles containing the drug and that these micelles are the entities which provide for penetration of the drug through the mucosa.

In some subjects, the fusidic acid derivative employed in the method of Carey et al. has exhibited mild irritation of the nasal tissues. The irritation is relatively mild by comparison with the discomfort associated with drug delivery by injection and varies considerably in degree from subject to subject. Furthermore, the irritation does not appear to be associated with significant, nontransient effects on the integrity of the intranasal mucosa. Nonetheless, it would be highly desirable to provide a composition for transmucosal drug delivery having the efficacy exhibited by the system of Carey et al., but without the concomitant irritation experienced by some subjects.

Another drawback associated with the compositions of Carey et al., as well as other systems for delivering proteins and polypeptides, is that they are, for the most part, aqueous systems. Unfortunately, proteins and polypeptides generally have limited stability in aqueous systems. Thus, it is necessary either to use the composition shortly after it is prepared or to provide the protein or peptide drug in lyophilized form for aqueous reconstitution at the time of use. Reconstitution of the composition is inconvenient and introduces the opportunity for errors in formulation or for the introduction of contaminants.

Another problem associated with intranasal delivery using aqueous systems results from the fact that they are usually applied by an applicator which provides mechanical pumping means for pumping the aqueous composition through a spray nozzle. The resulting spray pattern can vary considerably among individual users and from application to application, thus causing difficulty in controlling dosage.

It is an object of the present invention to provide compositions and methods for effectively administering pharmaceutically active substances, particularly protein or polypeptide drugs, across mucosal surfaces, without the mild irritation sometimes associated with prior art transmucosal delivery systems.

It is a further object of the invention to provide compositions and methods for administration of pharmaceutically active substances, particularly proteins or polypeptides, wherein the compositions have longer stability than aqueous compositions of the prior art and do not require reconstitution at the time of use.

It is yet a further object of the invention to provide compositions and methods for transmucosal delivery of pharmaceutically active substances which allow delivery of uniform dosage from subject-to-subject and application-to-application.

Other objects and advantages of the invention will become readily apparent from the disclosure which follows.

BRIEF DESCRIPTION OF THE INVENTION

The present invention provides methods and compositions for administering pharmaceutically active substances, particularly protein or polypeptide drugs, by transport across mucosal surfaces, e.g. intranasally. The invention is based on applicants' surprising discovery that the application to mucosal surfaces of certain amphiphilic steroids described by Carey et al., supra., in the form of non-aqueous, fluorocarbon- or hydrocarbon-based aerosol suspensions is not accompanied by any significant irritation of the type experienced by many subjects upon administration of the corresponding aqueous-based delivery systems. Furthermore, in animal models, the non-aqueous aerosol delivery system of the invention unpredictably provided greater bioavailability of the drug than aqueous systems using amphiphilic steroids as permeation enhancers.

In accordance with the present invention, there is provided a composition for the administration of a pharmaceutically active substance comprising:

(a) a medically effective amount of a pharmaceutically active substance;

(b) a biocompatible, amphiphilic steroid of the formula wherein a dashed line represents a single or double bond;

D represents a group having a molecular weight below 600 daltons which renders an effective amount of said steroid water soluble within the range of about pH 2 to about pH 12;

E represents OAc, OH, a lower alkyl group or a lower heteroalkyl group;

G represents OAc, OH, a lower alkyl group or a lower heteroalkyl group;

W represents OAc or H; and

Q, V and X each, individually, represent OH or H, said steroid (i) containing two to three polar functions, exclusive of the function represented by D; and (ii) being capable of increasing the permeation of a human or animal mucosal surface by a pharmaceutically active substance in an amount effective to increase the permeability of said body surface to a pharmaceutically active substance; and (c) a biocompatible (hydro/fluoro)carbon propellant.

In a preferred embodiment of the invention, E represents $\beta$-OAc, $\alpha$-OH, a lower alkyl group in the $\beta$-position or a lower heteroalkyl group in the $\alpha$- or $\beta$-position, G represents $\alpha$-OAc, $\alpha$-OH, or an $\alpha$-lower heteroalkyl group; W represents $\alpha$-OAc or H; Q represents H or OH; V represents H or $\alpha$-OH; and X represents H or $\alpha$-OH. (As used herein, the symbol "OAc" refers to the acetoxyl radical $OCOCH_3$).

In another embodiment of the invention, there is provided a method of administering a pharmaceutically active substance to a human or animal subject in need of such administration which comprises applying the aforesaid composition to a mucosal body surface in the form of an aerosol spray.

In yet another embodiment of the invention, there is provided a method for producing a composition for the administration of a pharmaceutically active substance. In accordance with this embodiment, an aqueous solution is prepared containing the biocompatible, amphiphilic steroid described above and the pharmaceutically active substance. Water is removed, for example by lyophilization, to produce particles in which the biocompatible amphiphilic steroid and the pharmaceutically active substance are intimately interspersed. The particles are then admixed with a normally-gaseous (hydro/fluoro)carbon propellant under sufficient pressure or low temperature that the (hydro/fluoro)carbon is in liquid form.

BRIEF DESCRIPTION OF THE INVENTION

DETAILED DESCRIPTION OF THE INVENTION

As previously indicated, the composition of the invention for administering a pharmaceutically active substance contains a biocompatible, amphiphilic steroid. In general, the steroid can be any of the biocompatible, amphiphilic steroids described in U.S. Pat. No. 4,746,508 the disclosure of which is incorporated herein by reference. The steroid is preferably a derivative of fusidic acid or cephalosporin $P_1$, most preferably a derivative having formula (I), above. These steroid molecules are all characterized in that they have the specific four-ring structure of fusidic acid and cephalosporin $P_1$, including the boat conformation of the B ring (in contrast to cholesterol derivatives such as bile salts, which have the B ring in the lower energy, more stable chair conformation). The steroid of formula (I) can be unconjugated, e.g. D is $O^-Na^+$, $O^-Rb^+$, $O^-Cs^+$, or some other ionic configuration, or it can be conjugated at $C_{21}$, i.e. D is an organic group containing at least one carbon atom.

The conjugation group can be, e.g. any ionic function-containing straight or branch-chained amino acid. The amino acid can be aliphatic or aromatic, and can also be a homo- or a dihomo- amino acid, e.g. homotaurine or homoglycine, or an amphoteric amino acid, e.g., sulfobetaine or phosphobetaine. A straight or branched chain di- or tripeptide which terminates in an ionic function which is dissociated within the range from about pH 2 to about pH 12 can also be employed. Peptides larger than tripeptides generally should not be used because they can unacceptably lower solubility. Any suitable uronic acid, e.g. glucuronic acid, can also be used.

Preferred conjugating amino acids are glycine and taurine. Preferred straight-chain peptides are diglycine and glutathione, and preferred branched chain peptides are sarcosylcysteine, hydroxyprolinetaurine, and sarcosyltaurine.

When the conjugating group is a polyether of at least sixteen carbon atoms, the group need not (although it can) contain an ionic function; the ionic function is unnecessary because such groups are highly polar and thus confer solubility without ionization. For smaller polyether groups, an ionic function is generally necessary, although it can be weakly ionizable since the smaller polyethers are polar themselves. Preferably group D has a molecular weight below 600 daltons and is one of the following groups:

(A) a peptide of one, two, or three amino acids and containing an ionic function which is dissociated within the range of about pH 2 to about pH 12;

(B) a heteroalkyl group of three or fewer carbon atoms which contains an ionic function which is dissociated within the range of about pH 2 to about pH 12;

(C) a uronic acid of six or fewer carbon atoms which contains an ionic function which is dissociated within the range of about pH 2 to about pH 12;

(D) a polyether containing between six and fourteen carbon atoms, inclusive, which terminates in an ionic function which is dissociated within the range of about pH 2 to about pH 12; or (E) a polyether containing between sixteen and twenty-four carbon atoms, inclusive, and optionally terminating in an ionic function which is dissociated within the range of about pH 2 to about pH 12.

The group bonded to each of $C_6$ and $C_{16}$ independently, (W and E in formula [I]) can be OAc ($OCOCH_3$) as in naturally occurring fusidic acid and cephalosporin $P_1$. Alternatively, E can be an alkyl (e.g., methyl or ethyl) or a different heteroalkyl (e.g. alkyloxy, alkylthio, or ether derivative) group of three or fewer carbon atoms; larger groups should not be used because they can unacceptably lower solubility. Group G, bonded to $C_3$, can be OH, as in naturally occurring fusidic acid and cephlosporin $P_1$. G can also be OAc, a lower alkyl group, or a different lower heteroalkyl group. Group W, if OAc, should be in the $\alpha$-position.

The molecule should possess two or three polar functions, exclusive of any side chains at $C_{21}$, at the positions indicated above where acetoxyl and hydroxyl groups can be located. The molecule can contain up to three OH groups, provided that, if three are present, one is $C_{16}\alpha$-axial replacing OAc at that position.

Preferably the steroid used in the invention is characterized in that the unconjugated derivative of the steroid is retained on a hydrophobic column for a length of time sufficient to produce a k' factor value of at least about 4, the k' factor value being obtained by subjecting a monomeric solution of 1 mg/ml of such steroid derivative to high-performance liquid column chromatography at 3,000 psi, using a 250×4.6 mm column having octadecylsilane-coated 5 μm silica particles as the stationary phase and a mobile phase, delivered at 1.0 ml/min., consisting of 75% methanol in water, v/v, buffered with 0.005M $KH_2PO_4/H_3PO_4$ to give an apparent pH value, as measured using a glass electrode, of 5.0, the k' factor value being defined by $$\kappa = \frac{t_r - t_0}{t_0},$$

where $t_0$ is the retention time in the column of the solvent front and $t_r$ is the retention time in the column of the steroid derivative as measured by obtaining the elution profile of the steroid derivative by absorbance at 210 nm.

Preferably the steroid is further characterized in that the critical micellar temperature (CMT) (the temperature at which the steroid ceases to be an insoluble crystal or gel and begins to go into solution and self-associate in solution) of an aqueous 1% solution, w/v, of the steroid is below human or animal body temperature, and optimally below about 0° C. within the range of about pH 2 to about pH 12 (a measure of solubility); and the critical micellar concentration (CMC) (the concentration at which the steroid ceases to be an ideal solution and begins to self-associate) is as high as 40 mM but preferably less than 15 mM, and more preferably less than 4 mM at 37° C. in 0.15 M NaCl as measured by surface tension.

Whenever it is specified herein that the steroid molecule has an indicated property "within the range from about pH 2 to about pH 12", it is not required that the molecule possess the indicated property over the entire range, but rather, that it possess the indicated property within a portion of that pH range at which the formulation is to be prepared.

Preferred steroids are ionized or partially ionized alkali salts of fusidic acid, 24,25-dihydrofusidic acid, tauro-24,25-dihydrofusidate and g)yco-24,25-dihydrofusidate. A highly preferred steroid for use in the composition and method of the invention is sodium tauro-24,25-dihydrofusidate.

Any of the fusidic acid or cephalosporin $P_1$ derivatives are made by appropriately modifying commercially available fusidic acid or cephalosporin $P_1$. Such techniques are well known and are described, e.g. in U.S. Pat. No. 4,315,004, hereby incorporated by reference.

The term "pharmaceutically active substance" as used herein refers to any substance which is useful in the prevention or treatment of disease or injury or in the regulation of a physiological condition in a human or animal subject. The pharmaceutically active substances which can be incorporated into the compositions of the invention preferably have a molecular weights between about 100 and 300,000. A preferred class of pharmaceutically active substances for delivery by the method of this invention are polypeptides and proteins. As hereinafter used, the term "polypeptide" shall refer to any compound containing two or more amino acid moieties linked by peptide bonds, whether such compound has a molecular weight which would normally cause it to be referred to as a "protein" (i.e. a molecular weight above about 10,000 daltons) or a molecular weight which would normally cause it to be referred to as a "peptide" or "polypeptide" (i.e. a molecular weight below about 10,000 daltons). Furthermore, the term "polypeptide" is intended to encompass not only the native forms of the polypeptide in question but also modifications of the native forms which retain qualitatively the biological activity of the corresponding native protein or which may enhance biological activity, including for example acid or base addition salts, amides or esters and modifications or deletion of the glycosylation pattern of the native polypeptide. Also included are biologically active fragments or analogues of polypeptides known to have biological activity.

There is a veritable host of useful polypeptides which can be incorporated into the compositions of the invention. One can mention, as merely illustrative thereof, hormones such as insulin, insulinotropin, glucagon, human and animal growth hormones, luteinizing hormone, luteinizing hormone releasing hormone, follicle stimulating hormone, LHRH analogues, human and animal calcitonins such as salmon calcitonin, eel calcitonin and chicken calcitonin, growth hormone releasing hormone, corticotropin releasing hormone, somatostatin, somatomedin, parathyroid hormone, chorionic gonadotropin, vasopressin, renin, corticotropin, erythropoietin, prolactin and cholecystokinin and derivatives thereof such as sincalide; immune system modulators such as colony stimulating factor, interleukin-1, interleukin-2, $\alpha$-, $\beta$- and $\gamma$-interferons, complement D and other proteins of the complement pathway; polypeptides which affect(the neurological system, such as enkephalins, endorphins and delta sleep inducing peptide; and polypeptides that regulate metabolism such as human or animal adipsin.

The compositions of the invention can also incorporate non-peptide drugs including the known drugs which exhibit limited bioavailability when delivered through the gastrointestinal tract; e.g. drugs affecting the cardiovascular, renal, metabolic, hepatic, pulmonary and immune systems. Non-peptide drugs which can be administered include narcotic and non-narcotic analgesics, anti-inflammatory agents, antihypertensives, antibacterials and antivirals. Another group of non-peptide drugs deliverable by the method of the invention is water insoluble, fat-soluble hydrophobic drugs, e.g. steroids such as progesterone, estrogens, androgens and their analogs.

The compositions of the invention contain a (hydro/fluoro)carbon propellant. The term "(hydro/fluoro)carbon" is intended to encompass hydrocarbon molecules or fluorocarbon molecules or carbon-based molecules containing both hydrogen and fluorine substituents, as well as mixtures of such molecules. The propellant must be biocompatible and inert to the active components of the composition. The propellant must be normally-gaseous, that is gaseous at atmospheric pressure and ambient temperature, but capable of being compressed to a liquid at pressures employed by conventional pressure-fill equipment used in the pharmaceutical industry. Preferred propellants which meet these requirements and which are commercially available are fluorocarbons that can be defined by the formula $C_nH_xCl_yF_z$ in which n is an integer from 1 to 4, preferably 1 or 2; x, y and z are integers such that the sum of $x+y+z$ equals $2n+2$, the sum of $y+z$ is at least 2 and z is greater than zero. Fluorocarbon propellants of this type are commercially available, for example, under the trademark Freon® (E. I. DuPont DeNemours & Co., Wilmington, Del.). Particularly preferred fluorocarbon propellants or use in the compositions of the invention are the compounds $CCl_3F$ and $CCl_2F_2$ or mixtures of the two. These compounds are commercially available under the designations Freon®-11 and Freon®-12.

If desired, low molecular weight hydrocarbon propellants can also be employed in the compositions and these may even be more acceptable from an environmental point of view. Preferred hydrocarbon propellants are propane, isobutane and butane.

Figure 1:
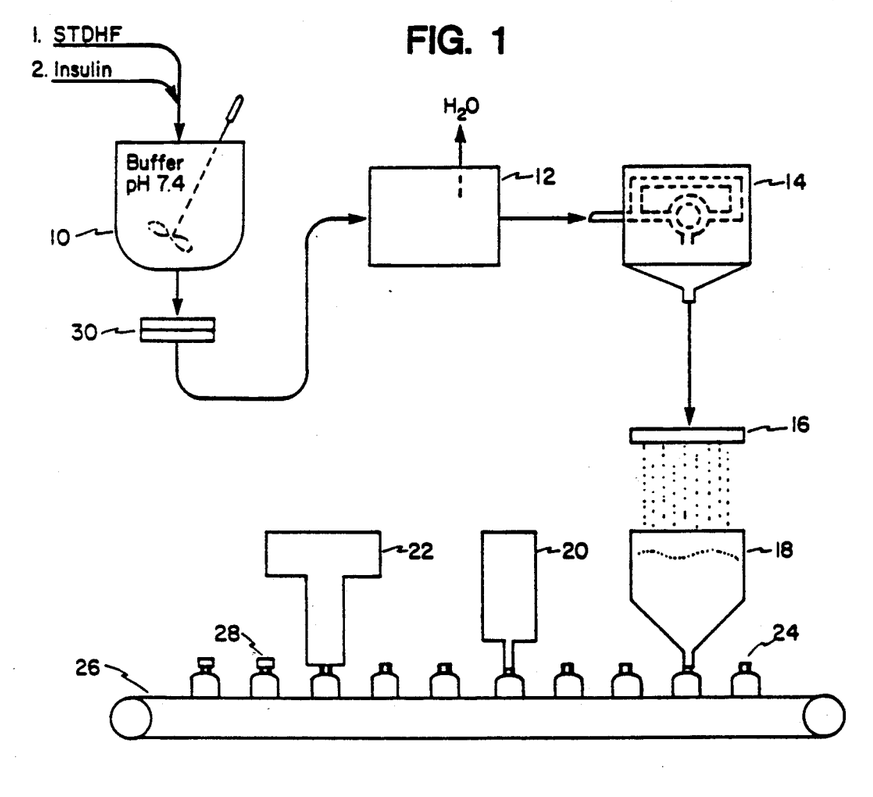
FIG. 1 is a schematic flow diagram illustrating a preferred embodiment of the method of the invention for producing a composition for pharmaceutical administration.

The composition of the invention is prepared by a process which can be understood by reference to the diagram in FIG. 1. The schematic specifically illustrates the preparation of a composition in which sodium tauro-24,25-dihydrofusidate (STDHF) is the steroid component and insulin is the pharmaceutically active substance. It will be understood, however, that the illustrated process is equally applicable to the preparation of compositions employing other steroid permeation enhancers of formula I and other pharmaceutically active substances.

Referring to the figure, STDHF is dissolved in a buffer, e.g. phosphate buffer, at physiologic pH, i.e. from about 5.0 to 8.0, preferably about 7.4, in a suitable mixing vessel 10 equipped with temperature control means. Insulin is added and then the temperature is elevated to enhance solubility, i.e. from about 30° C. to 40° C., preferably about 37° C. for about 10 min. The temperature of the solution or buffer can be elevated to varying degrees, if necessary, to enhance dissolution if other pharmaceutically active substances are employed, with the particular pH and temperature being determined large)y by the solubility characteristics of the pharmaceutically active substance.

The STDHF/insulin solution is filtered, e.g. by passing it through a 0.2 $\mu$m filter 30, and transferred to a freeze dryer 12, where water is removed under vacuum to produce a lyophilized cake. The lyophilized cake is then transferred to a suitable device for comminution, such as an air attrition mill 14. The comminuted material preferably has a particle size from about 1 micron to about 45 microns. The preferred particle size may vary depending on the desired locus of administration. For intranasal administration, a particle size from about 5 microns to about 40 microns is preferred, whereas for administration through the bronchopulmonary system, a particle size from about 2 microns to about 8 microns is preferred. The comminuted material is sized to remove oversize particles by passing it through a sieve 16, preferably having a mesh size of about 325 mesh. The sized powder is transferred to a conventional device for metering dry powder materials 18. The desired quantity of powder is metered into sterile containers 24, such as glass or aluminum vials. The containers 24 are transferred, for example by conveyor 26, to a pressure filling device or cold filling device 20 where they are filled with (hydro/fluoro)carbon propellant, from a propellant source (not shown), under sufficient pressure or low temperature such that the propellant is in a liquid state, and the containers 24 are passed to a capping station 22, where they are crimped and capped with an aerosol valve 28. Alternatively, e.g. where the solid content is low, one may add the lyophilized particulate to bulk liquid propellant in a pressurized tank. This suspension can then be metered into individual containers. Suitable equipment for pressure filling or cold filling, crimping and capping is widely commercially available.

The composition in the container 24 comprises a suspension of finely divided particles in which the biocompatible amphiphilic steroid and the pharmaceutically active substance are intimately interspersed. The weight ratio of steroid to pharmaceutically active substance is from about 0.02 to about 20. The amount of pharmaceutically active ingredient in the composition will vary considerably, depending on the specific substance being delivered, the condition being treated, prevented or regulated, and the desired dosing regimen. For example, insulin would be administered in amounts effective for the treatment of diabetics; human or animal calcitonin in amounts effective for the treatment of Paget's disease or osteoporosis; human growth hormone in amounts effective for the treatment of pituitary dwarfism; and erythropoietin in amounts effective for the treatment or anemia. Generally, the pharmaceutically active substance can be present in the suspension in an amount from about 0.001% to about 5% (w/v). The biocompatible, amphiphilic steroid is generally present in amounts from about 0.01% to about 5% (w/v).

If desired, optional ingredients of a conventional nature can also be present in the compositions of the invention. For example, adjuvants which facilitate the formation of lyophilized cake, such as mannitol or glycine, can be present in the known effective amounts. Generally, however, such adjuvants will not be required. Surprisingly, we have discovered that the presence of effective amounts of the steroid of formula I allows one to lyophilize peptides and proteins (e.g. insulin and human growth hormone) producing uniformly distributed solid matrices without the requirement of bulking agents such as mannitol and glycine or cryoprotectants such as bovine serum albumin. These uniform solid matrices are easily crushed to fine powders which are highly suited for use in dry aerosol formulations such as the composition of the invention. Furthermore, lyophilized powders produced from protein and steroid of formula I do not require the addition of lubricants such as oleic acid to prevent clogging of aerosol spray valves. In the case of polypeptide drugs, polypeptide stabilizing adjuvants generally are not required due to the highly stable nature of the polypeptide in non-aqueous suspension. Nonetheless, one may, if desired, include known protein stabilizing substances, such as ethylenediamine tetraacetic acid or its salts, in the usual known effective amounts.

The compositions of the invention can be used to treat, prevent or regulate a wide variety of conditions. Because of the low level of irritation to the mucosal tissues, it is possible to administer the compositions of the invention on a frequent basis with minimal discomfort to the patient. This is particularly important in the case of insulin delivery. The pharmacokinetics of insulin delivery via the compositions of the invention mimic the pulsatile nature of insulin release which follows the ingestion of food in normal subjects much more closely than does subcutaneous injection of insulin. Accordingly, the compositions of the invention are highly advantageous for delivering insulin, since the insulin can be delivered in a pulsatile manner following meals as often as is necessary without causing patient discomfort.

Another advantage of the particulate suspensions of the invention over aqueous compositions of the prior art is that it may be possible to deliver bioequivalent dosages of pharmaceutically active ingredient using less of the steroid permeation enhancer per unit dose. This is because the limited amount of moisture present in mucosal tissue allows relatively small amounts of the steroid to achieve a sufficiently high concentration upon contact with the mucosal surface to enhance permeation across the mucosal surface.

The compositions of the invention are used by spraying the composition, in the form of an aerosol, onto a mucosal surface of the body. Since the compositions are generally in the form of a suspension, it is desirable to agitate slightly the compositions, such as by shaking the container prior to administration, in order to assure a uniform suspension at the time of application. If desired, beads (e.g. glass beads) may be placed in the container to break up any agglomerates of the suspended particles. The preferred route of delivery is intranasal, however, the compositions may be applied to other mucosal surfaces such as the surfaces of the bronchopulmonary system, vaginal or rectal surfaces. Preferably, the container from which the composition is dispensed is fitted with a metering chamber which is in communication with the spray valve to dispense a metered amount of aerosol each time the valve is actuated. Metered dispensing devices of this type are well known in aerosol technology. The metered amount which is delivered can vary considerably, depending on the concentration of pharmaceutically active ingredient, the desired dosing regimen and the approximate surface area of the mucosal surface to which the composition is applied. The aerosol suspensions of the invention generally can be applied in a more consistent and uniform spray pattern then the aqueous solutions of the prior art.

The following examples are intended to illustrate further the practice of the invention and are not intended to limit its scope in any way.

EXAMPLE I

Preparation of aerosol formulation for insulin administration.

A solution was prepared by admixing 60 mg of sodium tauro-24,25-dihydrofusidate (STDHF) with 6 ml of 20mM sodium phosphate buffer (14.4 mg) at pH 7.4 followed by the addition of 54.3 mg of zinc insulin. The solution was heated to 37° C. for ten minutes, filtered and freeze dried on an Edwards SO8 lyophilizer. A suspension was prepared by suspending 128.7 mg of lyophilized powder in 6 ml of a mixture consisting of 3 parts by weight $CCl_3F$ to 1 part by weight $CCl_2F_2$. The suspension stored in 6 ml aluminum container with a valve calibrated to deliver a 100 μl spray.

Example II

Nasal administration of insulin to sheep.

The composition of Example I was administered intranasally to sheep to determine its bioavailability. As a control, there was prepared an aqueous solution of insulin and STDHF. The control ($IN_{solution}$) solution was prepared by solubilizing STDHF (10 mg/ml) in 20mM sodium phosphate buffer. Zinc insulin (2.26 mg/ml) was added and the solution was heated to 37° C. for ten minutes to solubilize the insulin. The solution was filtered and stored in a metered dosage sprayer at 4° C.

The sheep used in the experiment weighed approximately 37 kg ±5 kg. Six sheep were used for each dose. After dosing, the sheep were allowed to recover for 48 hours prior to the next administration. On the first day of the experiment sheep Nos. 1–3 were administered the insulin via the control formulation ($IN_{solution}$) and sheep Nos. 3–6 received insulin via the aerosol formulation of Example I ($IN_{aerosol}$). On the third day the order was reversed.

Twenty-four hours prior to dosing, an indwelling catheter was inserted into the right jugular vein, fixed with adhesive, and flushed with 5 ml of sterile 20mM phosphate buffer with 0.15 M NaCl added. The catheter was left in place for the duration of the experiment. Sheep were fasted overnight and weighed on the morning of the experiment. Ten minutes prior to administration the sheep were anesthetized with Ketamine HCl administered through the indwelling catheter.

The $IN_{aerosol}$ dose was not adjusted to the weight of the animal. Each sheep received 100 $\mu$l of $IN_{aerosol}$ spray in each naris through an 8 cm extension tube attached to the spray valve.

The $IN_{solution}$ dose was adjusted for the weight of each sheep (8 $\mu$l/kg into each naris) administered as drops with a P-1000 pipetman using a 7 cm polyethylene (1 mm i.d.) nasal delivery catheter attached with rubber cement to a micropipet tip. The volume range of 256 to 336 $\mu$l (32-42 kg) per nostril was delivered to the ventral nasal meatus at a distance of 7 cm from the anterior nares.

Table 1 summarizes the administered dosages of each formulation.

TABLE 1

| Formulation | [Insulin] mg/ml | [STDHF] mg/ml | Total Adm. Vol. $\mu$l |
|---|---|---|---|
| $IN_{solution}$ | 2.26 | 10.0 | 512-672* |
| $IN_{aerosol}$ | 9.05** | 10.0** | 200 |

*Adjusted for sheep weight.
**Indicates amount of Insulin or STDHF in 1 ml of freon propellant.

For the aerosol nasal spray, an 8 cm extension tube was inserted 6 cm into the ventral nasal meatus and a 100 $\mu$l spray was administered in each nostril. The total freon propellant volume administered to each sheep was 200 $\mu$l. Blood samples (5 ml) were drawn at the following time points: −15, 0, 5, 10, 15, 20, 30, 60, 90, 120, 180 minutes. The blood samples were placed on ice, stored at 4° C. overnight to separate the serum. Samples were spun and divided equally into 2 aliquots and stored at −20° C. Serum samples were assayed using a Cambridge Medical Diagnostics Insulin RIA kit.

Figure 2:
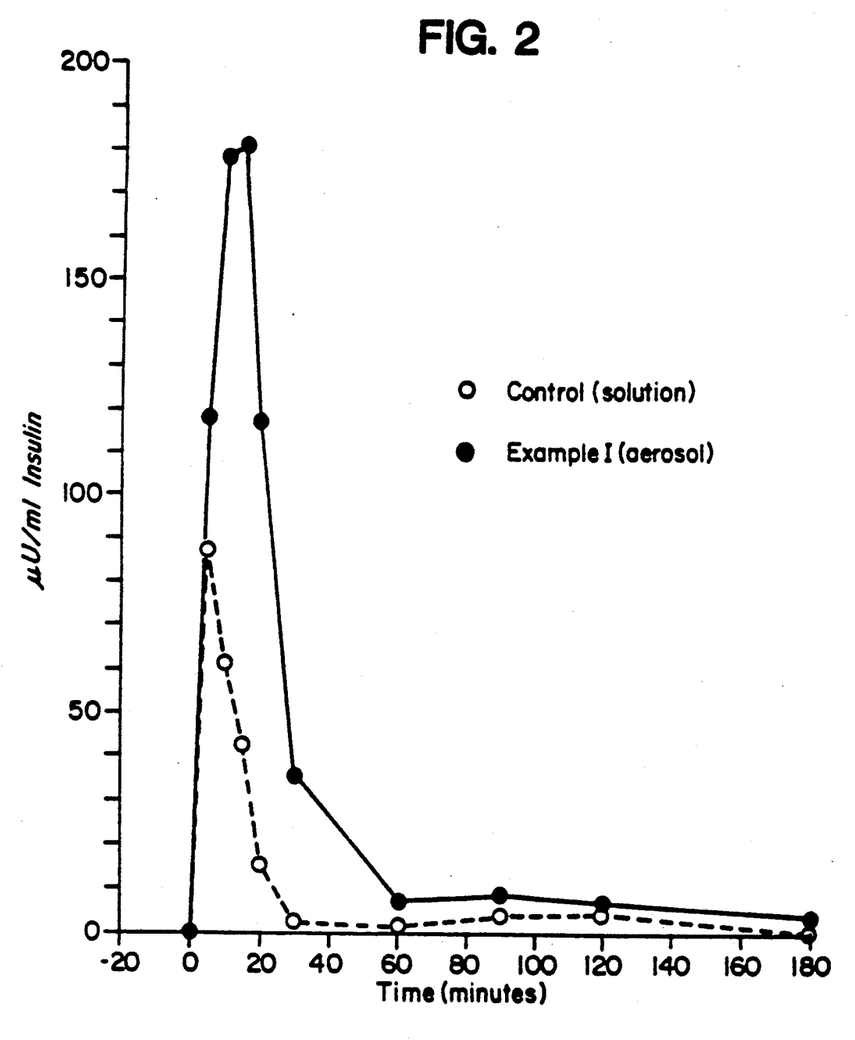
FIG. 2 is a graph presenting the average blood insulin levels for five of six sheep receiving insulin by the method of the invention and the six sheep receiving insulin in the form of an aqueous composition of the prior art.

FIG. 2 compares the average profiles of serum insulin concentration vs. time for the composition of Example 1 and the control formulations. Both curves decrease to baseline at 60 minutes, consistent with previous insulin sheep studies using aqueous based delivery systems similar to the control formulation. (Longenecker, et al., J. Pharm. Sci., 76, 351 [1987]. In calculating the area under the curve (AUC) values plotted in FIG. 2, the insulin levels at time point −15 minutes and zero were subtracted out for each animal. Average results are presented for only five of the six sheep receiving the aerosol formulation because the sixth sheep exhibited anomalously high blood levels. The area under the curve (AUC) for the average profiles of the solution and the aerosol formulations, including $T_{max}$ and $C_{max}$ are listed in Table 2.

The results of the insulin radioimmunoassay indicate that the bioavailability of the insulin aerosol formulation is greater than the solution formulation.

TABLE 2

| Formulation | [insulin] U/kg | AUC all pts | AUC −0 time pt. | $T_{max}$ minutes | $C_{max}$ $\mu$U/ml |
|---|---|---|---|---|---|
| Control (N = 6) | 1.00 | 5029.60 | 1486.70 | 5 | 69.84 |

TABLE 2-continued

| Formulation | [insulin] U/kg | AUC all pts | AUC −0 time pt. | $T_{max}$ minutes | $C_{max}$ $\mu$U/ml |
|---|---|---|---|---|---|
| Example I (N = 5) | 1.35 | 7308.90 | 3579.00* | 10-15 | 142.30* |

*Values normalized to correct for 1.35 U/kg dose in aerosol.

With the −15 minute and zero time point subtracted and [insulin] normalized there is a 2.3 fold increase in relative bioavailability for the aerosol composition of Example I as compared to the control solution formulation.

EXAMPLE III

Preparation of aerosol formulation for human growth hormone administration 30 mg of sodium-24,25-dihydrofusidate is solubilized in 6 ml of 10mM sodium phosphate buffer at pH 7.4. To this vehicle there is added 120 to 480 mg of human growth hormone with a bioactivity of 3 units/mg. The solution is rocked gently for 10 min. and then freeze dried on an Edwards SO8 lyophilizer. The resulting lyophilized powder is mixed with 6 ml of a liquid mixture of $CCl_3F$ and $CCl_2F_2$ (75:25) under pressure to form a suspension. The resulting suspension is applied by spraying 100 $\mu$l into each nostril, corresponding to a dose of 12 to 48 units of growth hormone per application.

EXAMPLE IV

Preparation of aerosol formulation for salmon calcitonin administration 30 mg of sodium-24,25-dihydrofusidate is solubilized in 6 ml of 20 mM phosphate buffer at pH 7.0. To this vehicle there is added 0.6 to 2.4 mg of salmon calcitonin having a bioactivity of 5,000 units/mg. The solution is freeze dried on an Edwards SO8 lyophilizer. The resulting lyophilized powder is mixed with 6 ml of a liquid mixture of $CCl_3F$ and $CCl_2F_2$ (75:25) under pressure to form a suspension. The resulting suspension can be used to treat osteoporosis or Paget's disease. It is applied by spraying 100 $\mu$l into each nostril, for a total dose of 100 to 400 units per application. Other forms of calcitonin may be substituted for salmon calcitonin with appropriate adjustments made for the relative bioactivity, e.g. eel calcitonin, chicken calcitonin, human calcitonin or elcatonin (synthetic eel calcitonin derivative).

EXAMPLE V

Preparation of aerosol formulation for human parathyroid hormone (1-34)

30 mg of sodium-24,25-dihydrofusidate is solubilized in 6 ml of 20 mM phosphate buffer at pH 7.0. To this vehicle there is added 0.3 to 3.0 mg of a peptide having the amino acid sequence of the N-terminal 34 amino acids of parathyroid hormone. The solution is freeze dried on an Edwards SO8 lyophilizer. The resulting lyophilized powder is mixed with 6 ml of a liquid mixture (75:25 p.b.w.) of $CCl_3F$ and $CCl_2F_2$ under pressure to form a suspension. The resulting suspension is useful in the treatment of osteoporosis. It is applied by spraying 100 $\mu$l of suspension into each nostril.

We claim:

1. A nonaqueous, dry powder composition for the transmucosal administration of pharmaceutically active substance, comprising a particulate suspension of:

(a) a medically effective amount of a polypeptide drug and
(b) a biocompatible steroid of the formula wherein a dashed line represents a single or double bond;

D represents a group having a molecular weight below 600 daltons which renders an effective amount of said steroid water soluble within the range of about pH 2 to about pH 12;

E represents OAc, OH, a lower alkyl group or a lower heteroalkyl group;

G represents OAc, OH, a lower alkyl group or a lower heteroalkyl group;

W represents OAc or H; and

Q, V, and X, each individually, represent OH or H, said steroid (i) containing two to three polar functions, exclusive of the function represented by D; and (ii) being capable of increasing the permeation of a human or animal mucosal surface by a pharmaceutically active substance, in an amount effective to increase the permeability of said body surface to a pharmaceutically active substance; and wherein said particulate suspension is suspended in a biocompatible (hydro/fluoro) carbon propellant.

2. A composition as claimed in claim 1, wherein the steroid has the formula:

wherein a dashed line represents a single or double bond;

D represents a group having a molecular weight below 600 daltons which renders an effect amount of said steroid water-soluble within the range of about pH 2 to about pH 12;

E represents $\beta$-OAc, $\alpha$-OH, a lower alkyl group in the $\beta$-position or a lower heteroalkyl group in the $\alpha$- or $\beta$-position;

G represents $\beta$-OAc, $\beta$-OH, or a lower heteroalkyl group in the $\alpha$-position;

W represents $\alpha$-OAc or H;

Q represents H or OH;

V represents H or $\alpha$-OH; and

X represents H or $\alpha$-OH, said steroid containing from two to three OH groups.

3. A composition as claimed in claim 1 wherein the biocompatible (hydro/fluoro)carbon propellant comprises at least one fluorocarbon compound of the formula $C_nH_xCl_yF_z$ in which n is an integer from 1 to 4; x, y and z are integers such that the sum $x+y+Z$ equals $2n+2$, the sum of $y+z$ is at least 2 and z is greater than zero.

4. A composition as claimed in claim 3, wherein n is 1 or 2.

5. A composition as claimed in claim 3 wherein the biocompatible fluorocarbon propellant comprises at least one compound selected from $CCl_3F$ and $CCl_2F_2$.

6. A composition as claimed in claim 1 wherein the biocompatible, amphiphilic steroid is sodium tauro-24,25-dihydrofusidate.

7. A composition as claimed in claim 1 wherein the pharmaceutically active substance is a polypeptide compound.

8. A composition as claimed in claim 7 wherein the polypeptide is selected from insulin, human growth hormone, luteinizing hormone releasing hormone, human or animal calcitonins, erythropoietin, and parathyroid hormone.

9. A composition as claimed in claim 7 wherein the polypeptide is insulin.

10. A composition as claimed in claim 1 in which the biocompatible, amphiphilic steroid and the pharmaceutically active substance are suspended in liquid (hydro/fluoro)carbon propellant in the form of particles in which they are intimately interspersed with each other.

11. A composition as claimed in claim 10 wherein the particles have a particle size from about 2 microns to about 45 microns.

12. A method of administering a particulate suspension of a pharmaceutically active substance which is substantially free of water, comprising applying to a mucosal body surface a particulate composition comprising:

(a) a medically effective amount of a pharmaceutically active substance; and
(b) a biocompatible steroid of the formula wherein a dashed line represents a single or double bond;

D represents a group having a molecular weight below 600 daltons which renders an effective amount of said steroid water soluble within the range of about pH 2 to about pH 12;

E represents OAc, OH, a lower alkyl group or a lower heteroalkyl group;

G represents OAc, OH, a lower alkyl group or a lower heteroalkyl group;

W represents OAc or H; and

Q, V, and X individually, represent OH or H, said steroid (i) containing two to three polar functions, exclusive of the function represented by D; and (ii) being capable of increasing the permeation of a human or animal mucosal surface by a pharmaceutically active substance, in a amount effective to increase the permeability of said body surface to a pharmaceutically active substance, wherein said composition is delivered to the body surface by means of a biocompatible (hydro/fluoro) carbon aerosol propellant.

13. A method as claimed in claim 12, wherein the biocompatible steroid has the formula:

wherein a dashed line represents a single or double bond;

D represents a group having a molecular weight below 600 daltons which renders an effect amount of said steroid water-soluble within the range of about pH 2 to about pH 12:

E represents $\beta$-OAc, $\alpha$-OH, a lower alkyl group in the $\be

G represents OAc, OH, a lower alkyl group or a lower heteroalkyl group;

W represents oAc or H; and

Q, V and X, each individually, represent OH or H, said steroid (i) containing two to three polar functions, exclusive of the function represented by D; and (ii) being capable of increasing the permeation of a human or animal mucosal surface by a pharmaceutically active substance in an amount effective to increase the permeability of said body surface to a pharmaceutically active substance; and

(ii) a medically effective amount of a pharmaceutically active substance;

(b) removing the water from the solution by lyophilization;

(c) sizing the lyophilized composition to a particle size from about 2 microns to about 45 microns; and (d) adding the lyophilized particulate to a normally-gaseous (hydro/fluoro)carbon propellant under sufficient pressure that the propellant is in liquid form.

28. A method as claimed in claim 27, wherein the biocompatible steroid has the formula:

wherein a dashed line represents a single or double bond;

D represents a group having a molecular weight below 600 daltons which renders an effect amount of said steroid water-soluble within the range of about pH 2 to about pH 12:

E represents $\beta$-OAc, $\beta$-OH, a lower alkyl group in the $\beta$-position or a lower heteroalkyl group in the $\alpha$- or $\beta$-position; position;

G represents $\alpha$-OAc, $\alpha$-OH, or a lower heteroalkyl group in the $\alpha$-position;

W represents $\alpha$-OAc or H;

Q represents H or OH;

V represents H or $\alpha$-OH; and

X represents H or $\alpha$-OH, said steroid containing from two to three OH groups.

29. A method as claimed in claim 28, wherein the biocompatible (hydro/fluoro)carbon propellant comprises at least one fluorocarbon compound of the formula $C_nH_xCl_yF_z$ in which n is an integer from 1 to 4; x, y and z are integers such that the sum of $x+y+z$ equals $2n+2$, the sum of $y+z$ is at least 2 and z is greater then zero.

30. A method as claimed in claim 29, wherein n is 1 to 2.

31. A method as claimed in claim 29, wherein the biocompatible fluorocarbon propellant comprises at least one compound selected from $CCl_3F$ and $CCl_2F_2$.

32. A method as c)aimed in claim 27, wherein the biocompatible, amphiphilic steroid is sodium-24,25-dihydrofusidate.

33. A method as claimed in claim 27, wherein the pharmaceutically active substance is a polypeptide compound.

34. A method as claimed in claim 33, wherein the polypeptide is insulin and the aqueous solution is prepared at elevated temperature to enhance dissolution.

35. A method as claimed in claim 33, wherein a buffer is added to the aqueous solution to maintain physiologic pH.

36. A composition for the administration of a pharmaceutically active a polypeptide drug, the composition comprising a lyophilized powder formulation of:

(a) a medically effective amount of the polypeptide drug and (b) a biocompatible steroid of the formula wherein a dashed line represents a single or double bond;

D represents a group having a molecular weight below 600 daltons which renders an effective amount of said steroid water-soluble within the range of about pH 2 to about pH 12;

E represents OAc, OH, a lower alkyl group or a lower heteroalkyl group;

G represents OAc, OH, a lower alkyl group or a lower heteroalkyl group;

W represents OAc or H; and

Q, V and X, each individually, represent OH or H, said steroid (i) containing two to three polar functions, exclusive of the function represented by D; and (ii) being capable of increasing the permeation of a human or animal mucosal surface by a pharmaceutically active substance, in an amount effective to increase the permeability of said body surface to a pharmaceutically active substance; and wherein said particulate suspension is suspended in a biocompatible (hydro/fluoro) carbon propellant.

37. A composition as claimed in claim 36 wherein the biocompatible (hydro/fluoro) carbon propellant comprises at least one fluorocarbon compound of the formula $C_nH_xCl_yF_z$ in which n is an integer from 1 to 4; x, y and z are integers such that the sum $x+y+z$ equals $2n+2$, the sum of $y+z$ is at least 2 and z is greater than zero.

38. A composition as claimed in claim 37 wherein n is 1 or 2.

39. A composition as claimed in claim 37 wherein the biocompatible fluorocarbon propellant comprises at least one compound selected from $CCl_3F$ and $CCl_2F_2$.

40. A composition as claimed in claim 36 wherein the biocompatible, amphiphilic steroid is sodium tauro-24,25-dihydrofusidate.

41. A composition as claimed in claim 36 wherein the polypeptide drug is selected from insulin, human growth hormone, luteinizing hormone releasing hormone, human or animal calcitonins, erythropoietin, and parathyroid hormone.

42. A composition as claimed in claim 41 wherein the polypeptide drug is insulin.

43. A composition as claimed in claim 36 wherein the powder formulation comprises particles of from about 2 microns to about 45 microns.

* * * * *